(12) United States Patent
Gomez et al.

(10) Patent No.: US 11,723,637 B2
(45) Date of Patent: Aug. 15, 2023

(54) METHOD AND APPARATUS FOR INTRA-ABDOMINAL ASSEMBLY, DISASSEMBLY AND RETRIEVAL OF LAPAROSCOPIC INSTRUMENTS

(71) Applicant: New Wave Endo-Surgery Inc., Coconut Creek, FL (US)

(72) Inventors: Ricardo Alexander Gomez, Lighthouse, FL (US); Sandy Lawrence Heck, Los Angeles, CA (US); Eric Allen Lopez, North Lauderdale, FL (US)

(73) Assignee: NEW WAVE ENDO-SURGICAL CORP., Coconut Creek, FL (US)

( * ) Notice: Subject to any disclaimer, the term of this patent is extended or adjusted under 35 U.S.C. 154(b) by 207 days.

(21) Appl. No.: 16/656,855

(22) Filed: Oct. 18, 2019

(65) Prior Publication Data
US 2020/0121309 A1    Apr. 23, 2020

Related U.S. Application Data

(60) Provisional application No. 62/748,123, filed on Oct. 19, 2018.

(51) Int. Cl.
| | | |
|---|---|---|
| A61B 1/313 | (2006.01) | |
| A61B 1/00 | (2006.01) | |
| A61B 17/00 | (2006.01) | |
| A61B 1/015 | (2006.01) | |

(52) U.S. Cl.
CPC .... *A61B 17/00234* (2013.01); *A61B 1/00121* (2013.01); *A61B 1/015* (2013.01); *A61B 1/3132* (2013.01); *A61B 2017/00358* (2013.01); *A61B 2017/00818* (2013.01)

(58) Field of Classification Search
None
See application file for complete search history.

(56) References Cited

U.S. PATENT DOCUMENTS

| | | | | |
|---|---|---|---|---|
| 5,163,942 A | * | 11/1992 | Rydell | A61B 17/32056 606/1 |
| 5,569,269 A | * | 10/1996 | Hart | A61B 17/0483 112/169 |
| 5,697,936 A | * | 12/1997 | Shipko | A61N 1/057 600/372 |

(Continued)

FOREIGN PATENT DOCUMENTS

WO    2012112622    8/2012

OTHER PUBLICATIONS

International Search Report issued in corresponding PCT Application No. PCT/US2019/056959 dated Jan. 6, 2020.

*Primary Examiner* — Michael J Carey
*Assistant Examiner* — Minqiao Huang
(74) *Attorney, Agent, or Firm* — Grogan, Tuccillo & Vanderleeden, LLP

(57) ABSTRACT

The present invention relates to a specialized laparoscopic device and method used for attachment of instrument heads to thin shafts in the abdomen of a patient. The device allows quick attachment of oversized instrument heads minimizing the scaring and recovery time of the patient. A specialized instrument head having a tether and a grabbing device are used to perform this process.

13 Claims, 13 Drawing Sheets

(56) References Cited

U.S. PATENT DOCUMENTS

| | | | | |
|---|---|---|---|---|
| 5,749,879 A | * | 5/1998 | Middleman | A61B 18/082 |
| | | | | 606/139 |
| 5,817,111 A | * | 10/1998 | Riza | A61B 17/06109 |
| | | | | 606/139 |
| 6,814,751 B2 | * | 11/2004 | Rosengart | A61B 17/11 |
| | | | | 623/1.23 |
| 8,685,039 B2 | * | 4/2014 | Little | A61B 17/221 |
| | | | | 606/127 |
| 11,083,362 B2 | * | 8/2021 | Schwarz | A61B 1/00066 |
| 2005/0070885 A1 | * | 3/2005 | Nobis | A61B 17/2909 |
| | | | | 606/1 |
| 2007/0038022 A1 | * | 2/2007 | Nakao | A61B 17/0469 |
| | | | | 600/104 |
| 2007/0239141 A1 | * | 10/2007 | Hartley | A61B 17/221 |
| | | | | 606/1 |
| 2008/0294175 A1 | * | 11/2008 | Bardsley | A61B 17/1285 |
| | | | | 606/113 |
| 2009/0157115 A1 | * | 6/2009 | Fleming | A61B 17/221 |
| | | | | 606/200 |
| 2009/0209947 A1 | | 8/2009 | Gordin et al. | |
| 2014/0005474 A1 | | 1/2014 | Farin et al. | |
| 2014/0336458 A1 | | 11/2014 | Belson et al. | |
| 2015/0359547 A1 | * | 12/2015 | Vale | A61M 1/84 |
| | | | | 606/115 |
| 2016/0213919 A1 | * | 7/2016 | Suwito | A61N 1/37205 |
| 2017/0231647 A1 | * | 8/2017 | Saunders | A61B 17/32056 |
| | | | | 606/113 |
| 2017/0245861 A1 | * | 8/2017 | Clark, III | A61B 17/12013 |
| 2017/0258483 A1 | | 9/2017 | Coe et al. | |
| 2017/0281261 A1 | * | 10/2017 | Shuros | A61B 18/148 |
| 2018/0116693 A1 | * | 5/2018 | Blanchard | A61B 17/3496 |
| 2019/0038410 A1 | * | 2/2019 | Machold | A61F 2/2445 |
| 2021/0162189 A1 | * | 6/2021 | Smith | A61B 17/29 |

\* cited by examiner

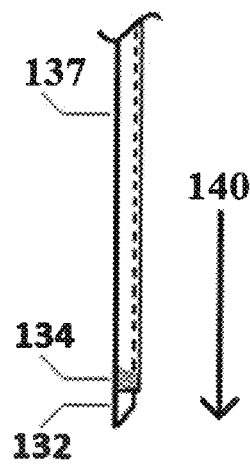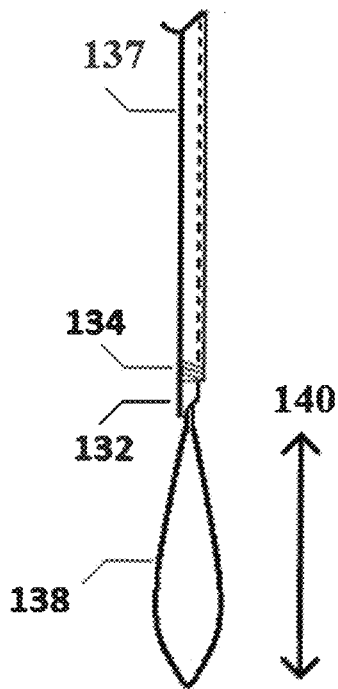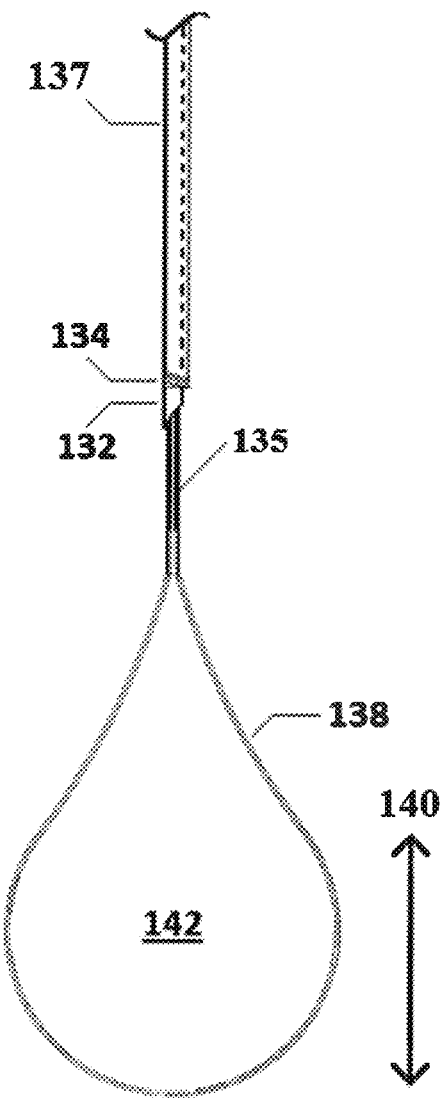
FIG. 3A
FIG. 3B
FIG. 3C

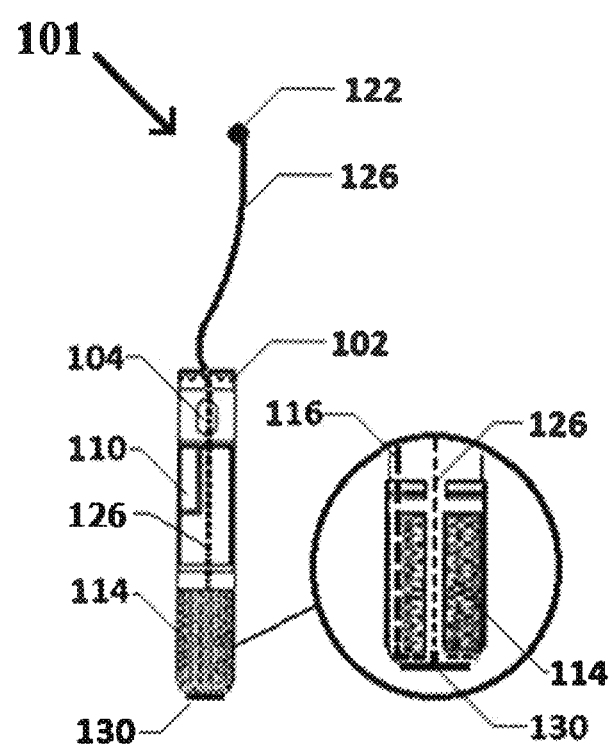
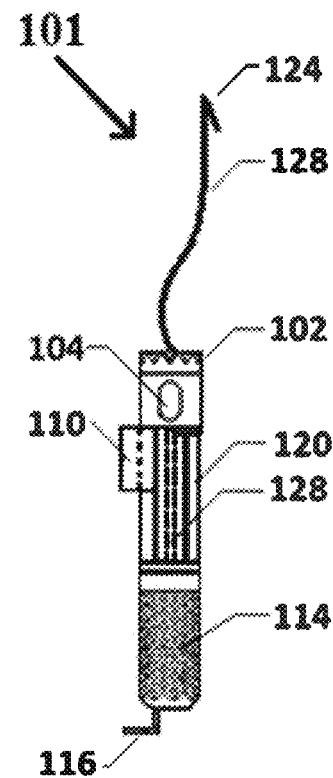
FIG. 6A                                FIG. 6B

METHOD AND APPARATUS FOR INTRA-ABDOMINAL ASSEMBLY, DISASSEMBLY AND RETRIEVAL OF LAPAROSCOPIC INSTRUMENTS

CROSS-REFERENCE TO RELATED APPLICATIONS

This application claims the priority benefit of U.S. Provisional Patent Application No. 62/748,123 filed on Oct. 19, 2018, titled "Method and Apparatus for Intra-Abdominal Assembly, Disassembly and Retrieval of Laparoscopic Instruments," naming the same inventors, and is hereby incorporated by reference for all that is disclosed as though fully set forth herein.

FIELD OF INVENTION

The present invention relates to methods and devices for performing minimally invasive surgical procedures involving specialized tool attachment methods and, in particular, to a specialized instrument head retrieval and removal system.

BACKGROUND OF INVENTION

Laparoscopic surgery provides several benefits to the patient related to the small shaft sizes of instruments, including smaller incision sizes, less pain, and quicker recovery after surgery. Unfortunately, laparoscopic instruments are limited in functionality by their small head sizes, and attempts to increase laparoscopic instrument head sizes usually require enlarging the shaft diameter, which negates the benefits of laparoscopic surgery.

In view of the above, there is a need for a system, method and apparatus that provides for the intra-abdominal assembly and retrieval of laparoscopic instruments and, in particular, for a device and method for use in laparoscopic surgical procedures whereby full function laparoscopic instrument heads can be coupled to thin shafts inside the body using minimally invasive techniques. In addition, there is a need in the field for a device that allows for the quick attachment of oversized instrument heads, which minimizes the scaring and recovery time of the patient, and which overcomes the common problems associated with clogging and other problems associated with longer surgical procedures.

SUMMARY OF INVENTION

The present invention is directed to a novel method and apparatus for attaching large, full function instrument heads to small shafts, so that the attachment and detachment process can be made more easily, thereby increasing surgeon adoption and bringing the benefits of small shafts and large instrument heads to a wider patient population.

In the present invention an instrument head is connected to the distal end of an instrument shaft by a novel method. In one aspect of the invention, the instrument head is brought into the body separately through an already established trocar port, such as the camera port. An instrument shaft having a lumen is inserted into the abdomen of a patient. A metallic wire assembly is inserted through the lumen of the instrument shaft. The metallic wire assembly is controlled by a wire loop tab, located at the proximal end of the instrument shaft. When the tab is pushed inward it causes the metallic wire assembly to move beyond the distal end of the instrument shaft. When the loop section of the wire assembly begins to exit from the distal end of the instrument shaft, the loop expands enabling it to engage/grab a tether or other feature attached to the instrument head. The wire assembly is then pulled back through the instrument shaft by the wire loop tab, causing it to collapse and pulling the tethered head with it. The tether is pulled completely through the lumen of the instrument shaft and out the other end. At this point the instrument head is drawn into position and locked onto the instrument shaft via a snap lock, threaded lock, or other similar locking feature. In an embodiment, a threaded portion on a distal end of the instrument shaft can be used to lock the instrument head in place. Other industry-recognized locking means can also be used.

In an embodiment, the metallic loop is a thin rigid wire that bends easily, but it also has the property of having rigidity to hold its shape and pick up the tether that is hanging out of the head. The expanded loop may take the shape of a diamond or oval shaped loop. The diamond shaped loop narrows in size to the point where it fits back into the instrument shaft and pulls the tether through it.

Once the tether is pulled it brings the instrument head into its locking position. The tether will extend through the proximal end of the shaft where it can be pulled free from the instrument head by a hard-pulling action, which exceeds the force required to lock the head onto the distal end of the shaft, at which point the distal end of the tether deforms and passes entirely through the head and out of the body through the instrument shaft.

The head can be removed from the shaft at the end of the procedure by several "unscrewing" methods in which the shaft is turned while the head is held in position. To remove the head, the grasper would hold the head in a designated spot and the shaft can be twisted to unscrew and separate the head from the shaft. The head can also be pulled up against the peritoneum and special friction inducing features can be employed to hold the head in position as the shaft is twisted and separated from the head.

An alternative method involves attaching the instrument head by using an instrument grasper. Its primary use is for attaching large instrument heads to small laparoscopic shafts, ex: 2 mm-5 mm, hereby an oversized instrument head is pushed through a patient's abdomen opening. A needle shaft is then inserted and using a standard bowel grasper, the instrument head is attached. The instrument head can incorporate a special zone or region designed for easily grasping the head without damaging its functionality. The grasper would push the head onto the shaft until it clicks.

To remove the instrument head, it is decoupled from the instrument shaft. Once the head is loose in the abdomen, it can be pulled out directly by a grasping instrument through an open trocar port, or in the preferred embodiment it can be pulled out with a magnetic retrieval system that is deployed through its own port or is preferably deployed through the camera port in a fashion that allows both the magnetic retrieval system and the camera to pass through the port simultaneously.

Other aspects and advantages of the present invention will become apparent from the following detailed description, which, when taken in conjunction with the accompanying drawings, illustrates by way of example the principles of the invention.

BRIEF DESCRIPTION OF DRAWINGS

The preferred embodiments of the invention will hereinafter be described in conjunction with the appended drawings provided to illustrate and not to limit the invention, in which:

FIG. 3A is an enlarged, side elevational view of a distal end of the instrument head retrieval-removal system, illustrating a retracted position of a grasping loop.

FIG. 3B is an enlarged, side elevational view the distal end of the instrument head retrieval-removal system, illustrating a partially-extended position of the grasping loop.

FIG. 3C is an enlarged, side elevational view the distal end of the instrument head retrieval-removal system, illustrating a fully-extended position of the grasping loop.

FIG. 6A is a side elevational view of the instrument head of FIG. 5, shown with a tether and knot.

FIG. 6B is a side elevational view of the instrument head of FIG. 5, shown with a metallic tether and hook.

Figure 1:
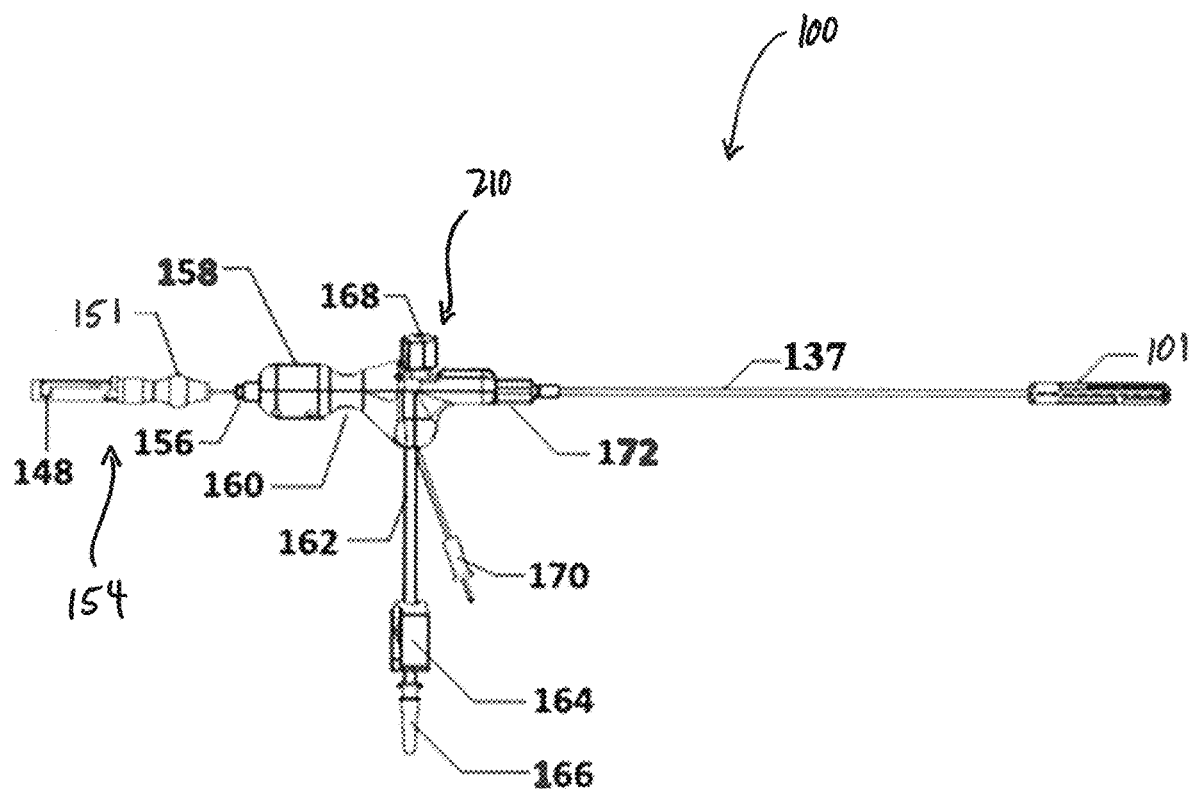
FIG. 1 is a side elevational view of an instrument head retrieval-removal system according to an embodiment of the present invention.

While the various features of this invention are hereinafter described and illustrated as being particularly adapted for providing rigidity to instrument devices the invention is not limited to the embodiments illustrated in the drawings but are merely used to illustrate the wide variety of uses of this invention. Therefore, the foregoing is considered as illustrative only of the principles of the invention. Since numerous modification and changes will readily occur by those skilled in the art, it is not desired to limit the invention to the exact construction and operation shown and described and accordingly, all suitable modifications and equivalents may be resorted to, falling within the scope of the invention.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

With respect to FIG. 1, an instrument head insertion and retrieval system (100) according to an embodiment of the present invention is shown. The system (100) is intended to be used in the field of laparoscopy, whereby instrument tools may be inserted and removed from the abdominal cavity (176) of a patient. As illustrated therein, the system (100) includes an instrument assembly (105), an instrument head retrieval device (154) slidably receivable within the instrument assembly (105) and an instrument head (101) connected to a distal end of the instrument assembly (105). The system (100) may further include an instrument head delivery and removal device (186) (not illustrated in FIG. 1) for the delivery/insertion and removal of the instrument head (101) into and out of the body of a patient, as disclosed hereinafter.

As shown in FIG. 1, the instrument assembly (105) includes body or handle portion (210) having a proximal end having a proximal opening (156) and a distal end having a coupling member (172), and an internal passageway (not shown) extending from the proximal end to the distal end. The instrument assembly (105) further includes a hollow outer shaft (137) connected to the distal end of the body (210) via the coupling member. In an embodiment, the proximal end of the outer shaft (137) may be threadedly attached to the body (210) via the coupling member (172) other means of attachment are also envisioned without departing from the broader aspects of the invention. In an embodiment, the outer shaft may be integrally formed with, or otherwise permanently attached, to the body (210).

Figure 2:
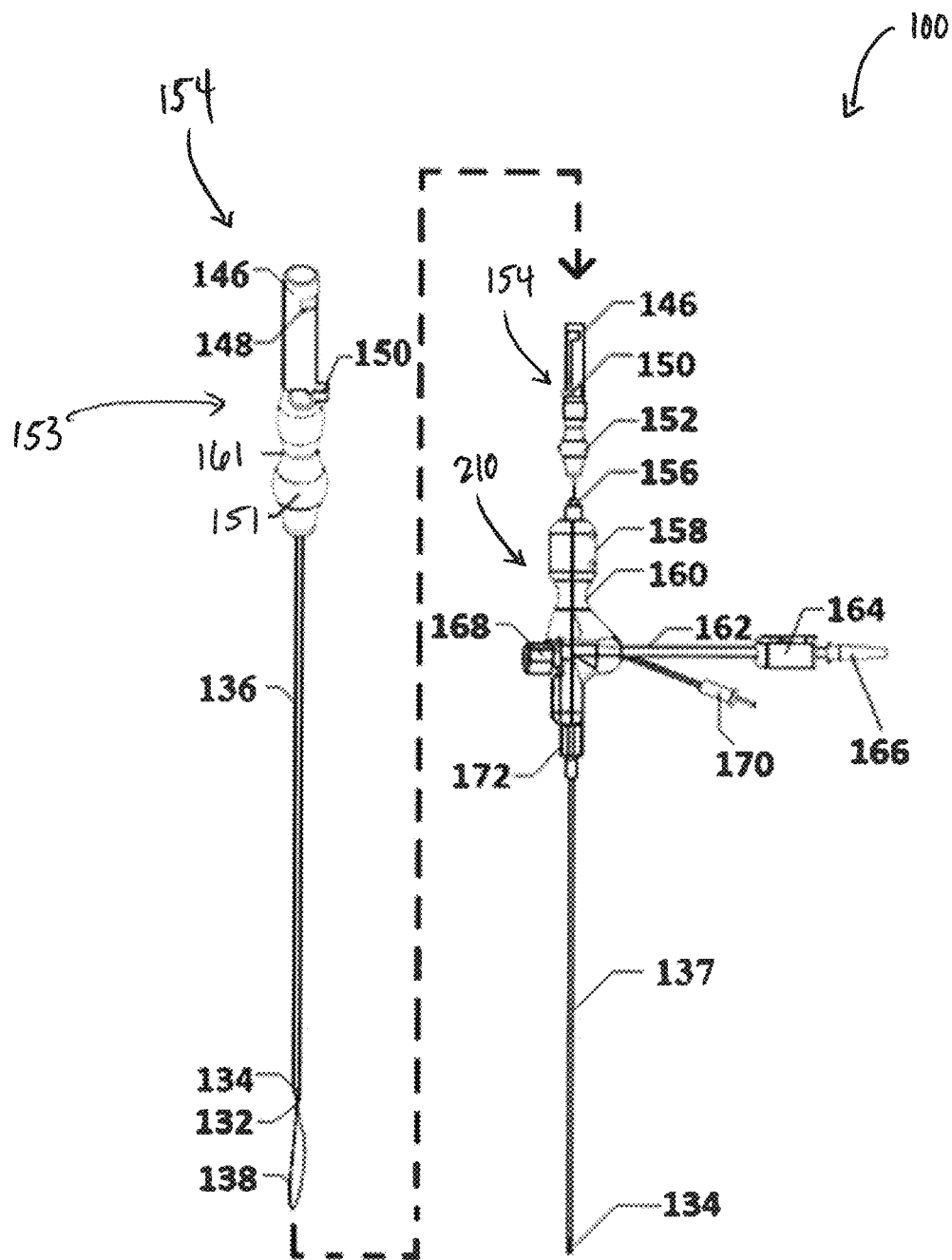
FIG. 2 side elevational, partial exploded view of an instrument head retrieval device of the instrument head retrieval-removal system of FIG. 1.

As best shown in FIGS. 1 and 2, the body or handle portion (210) of the instrument assembly (105) includes a balancing knob (158) adjacent to the proximal end which is used to hold the instrument assembly (105) securely, and a purlicue gripping/resting portion (160) used for resting the instrument assembly (105) on a user's hand. The balancing knob (158) is ergonomically designed/configured so that the user may hold it for long periods of time without straining the hand. As further shown therein, the instrument assembly (105) also includes a dually attached suction/irrigation hose (162) used for retrieving and expelling exudate and fluids during suctioning via selective fluid communication with the interior of the outer shaft (137). A pair of suction/irrigation knobs (168) on the body (210) are manually controllable to selectively provide suction and/or irrigation. The hose (162) may include a pinch clamp (164) which may be engaged to stop the flow of exudate and fluids being added or suctioned out. A distal end of the hose (162) may include a connector (166) (e.g., a tapered connector) for connecting the hose (162) to a suction and/or irrigation source. The instrument assembly (105) may also include an electrical connector (170) attachable to a source of electricity for provide current to an electrode of an attached instrument head (101) through the outer shaft (137).

With reference to FIGS. 1 and 2, the instrument head retrieval device (154) includes a handle portion (153) and a hollow inner shaft (136) connected to the handle portion (153). The handle portion (153) includes a knob (151) intended to facilitate gripping of the instrument head retrieval device (154) and a purlicue gripping/resting area (161) used for resting the device (154) on a user's hand. The device (154) also includes a generally hollow housing (146) connected to the handle portion (153) at a proximal end thereof, and having a generally L-shaped guide slot 148 formed in a sidewall of the housing (146). The interior of the housing (146) and interior of the shaft (136) define an interior space for receiving a spring-loaded piston and grasping member in the form of a loop. In particular, as best shown in the left side of FIG. 2, the retrieval device (154) includes a loop (138) connected to the spring loaded piston (not shown) by a shaft (135) that extends through the inner shaft (136) and handle portion (153). The spring loaded piston (not shown) has a tab actuator (150) that is movable within the slot (148) in the housing (146) to selectively move the piston up and down within the housing (148). As discussed in detail hereinafter, movement of the tab actuator (150) along the slot (148) effects selective movement of the loop (138) into and out of the inner shaft (136). As further shown in FIG. 2, in an embodiment, a distal end of the inner shaft (136) is magnetized and is threaded (either internally or externally), for the purposes discussed hereinafter, and is formed with a sharp, piercing tip (132).

As shown in FIG. 2, the inner shaft (136) of the instrument head retrieval device (154) is slidably receivable within the outer shaft (137) of the instrument assembly (105), i.e., by inserting the piercing tip (132) of the inner shaft (136) into the proximal opening (156) in the body (210) of the instrument assembly (105). Importantly, the inner shaft (136) of the retrieval device (154) is longer than a distance from the proximal opening (156) of the instrument assembly (105) to the distal tip of the outer shaft (137) of the instrument assembly (105), which ensures that the distal end of the inner shaft (136) extends beyond the distal end of the outer shaft (137) when the inner shaft (136) is fully received within the outer shaft (137). As illustrated in the right side of FIG. 2, the instrument head retrieval device (154) is slidably received by the instrument assembly (105) to form a single instrument/system.

Turning now to FIGS. 3A-3C, operation of the grasping loop (138) of the instrument head insertion and retrieval system (100) is illustrated. As shown in FIG. 3A, in a retracted position, the piercing tip (132) of the inner shaft (136) of the retrieval device (154) extends slightly beyond the distal end of the outer shaft (137) of the instrument assembly (105), and the grasping loop (138) is housed entirely within the inner shaft (136). The piercing tip (132) is used to insert the inner and outer shafts (136, 137) of the system (100) through the fascia and into the body of a patient. The grasping loop (138) is extendable from the inner shaft (136) by moving the tab (150) downwardly within slot (148), which correspondingly moves the piston, shaft (135) and loop (138) in the direction of arrow 140 in FIG. 3A. This movement causes the loop (138) to extend from the inner shaft (136), as illustrated in FIG. 3B. FIG. 3C illustrates the grasping loop (138) in its fully extended position, presenting a loop area (142) that is used to find an attach the instrument head (101), as disclosed hereinafter. (In FIGS. 3A-3C, arrow (140) illustrates possible directions of movement of the tab (150), piston, shaft (135) and loop (138)).

In an embodiment, the grasping loop may be formed from metal, although other materials known in the art may be utilized. Preferably, the loop (138) is a thin rigid, metallic wire that bends easily, but it also has the property of having rigidity to hold its shape and pick up the tether that is hanging out of the head. The expanded loop may take the shape of a diamond or oval shaped loop. The diamond shaped loop narrows in size to the point where it fits back into the instrument shaft and pulls the tether through it, as discussed below.

Figure 4A:
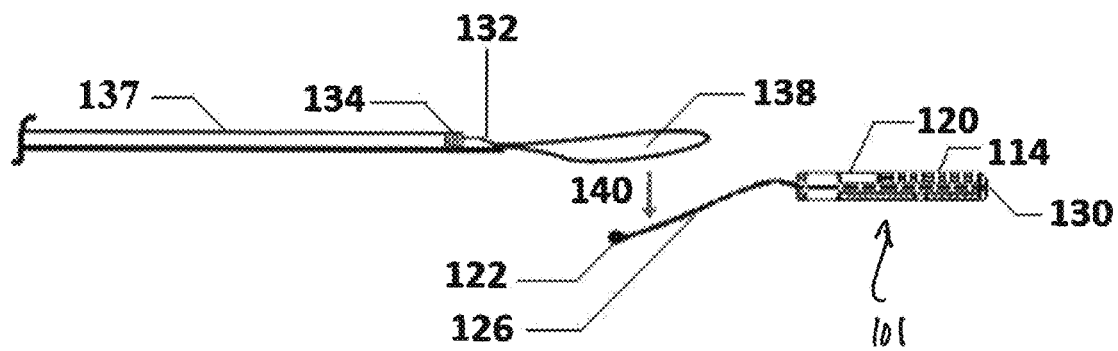
FIG. 4A is a side elevational view of the distal end of the instrument head retrieval-removal system properly positioned to begin attaching an instrument head.
Figure 4B:
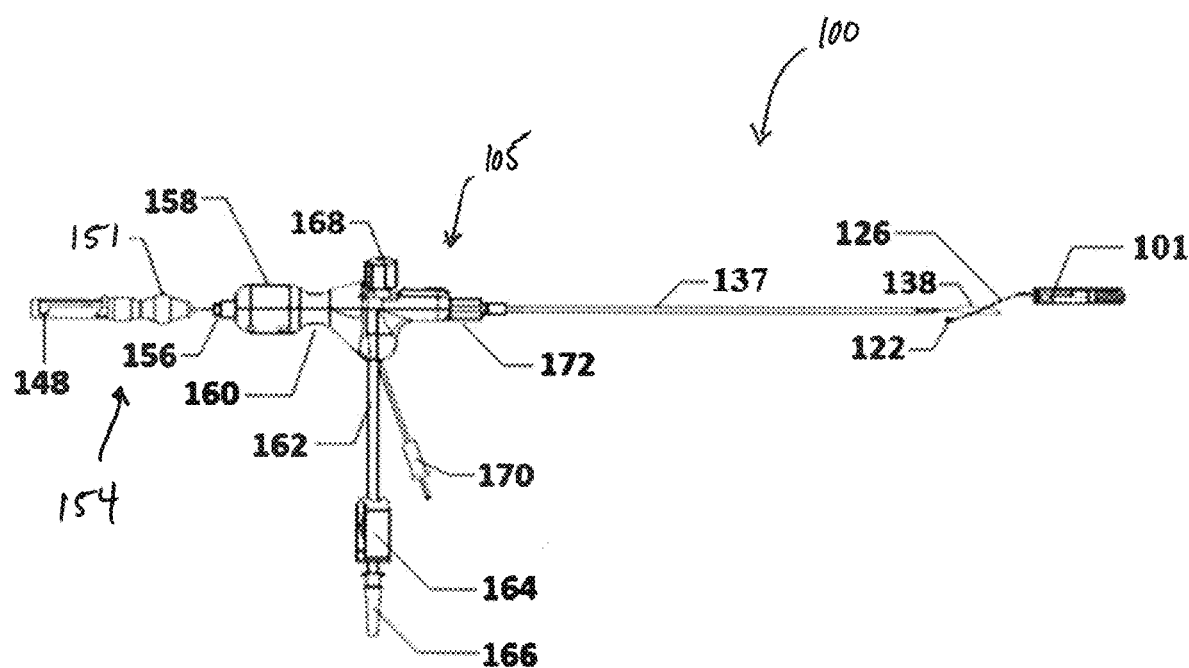
FIG. 4B is a side elevational view of the distal end of the instrument head retrieval-removal system showing a grasping loop properly looped over the string tether of the instrument head.

Turning now to FIGS. 4A and 4B, capture of the instrument head (101) is illustrated. As described hereinafter, the instrument head (101) may be separately inserted into the body of a patient through a trocar or other incision, and captured and attached to the instrument assembly (105) and or device (154) within the body of the patient. As shown in FIG. 4A, the instrument head (101) includes a body (120) having a proximal end and a distal end, a breakaway member (130) arranged at the distal end, and a tether (126) attached to the breakaway member (130) and extending from the breakaway member (130), through the body (120), and out of the proximal end where it terminates in an enlarged shoulder or stop, e.g., in the form of a knot (122).

In use, the loop (138), in its extended position, is moved over the knot (122) of the tether (126) in the direction of arrow (140), as shown in FIG. 4A, until the loop (138) engages the knot (122). The tab (150) is then moved upwardly within the slot (148), causing the loop (138) to retract within the inner shaft (136), pulling the tether (126) into the inner shaft (136) until the instrument head (101) abuts the distal end of the inner shaft (136). Importantly, the tether knot (122) is such dimensioned such that it will fit inside at least the outer needle shaft assembly (137) and preferably the inner shaft (136). FIG. 4B illustrates how the tether (126) and knot (122) are engaged by the loop (138).

Figure 5:
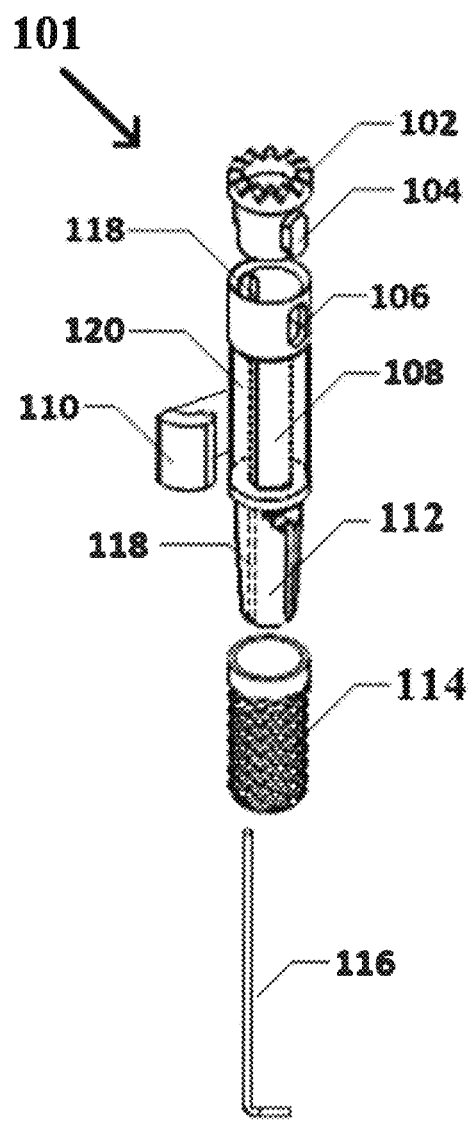
FIG. 5 presents an exploded, perspective view of an instrument head according to an embodiment of the present invention.

With reference to FIG. 5, the instrument head (101) according to an embodiment of the invention is illustrated. As shown therein, the instrument head (101) includes the body (120), which may be generally cylindrical in shape, a peanut shape retaining portion (112) on a distal end of the body (120), and a toothed connector (102) having an annular forward-facing toothed surface removably mounted to a proximal end of the body (120). In an embodiment, the toothed connector (102) is releasably mounted to the body (120) via a tab (104) that is received within a slot or window (106) in a sidewall of the body (120). As illustrated in FIG. 5, the instrument head (101) further includes a foam or absorbent member (114) received about the retaining portion (112). The foam (114) may be used to retain a lens cleaning solution for use in cleaning the lens of a laparoscope used during a surgical procedure, as known in the art. The instrument head (101) may additionally include a support member (108) that extends interior to the body (120) which imparts shape and rigidity to the instrument head (120). As also shown in FIG. 5, the instrument head (101) includes an electrode guide retainer (118) on an inner wall of the body (120) and which extends from the proximal end to the distal end, and an electrode (116) that is received in the guide retainer (118) and which extends from the distal end of the instrument head (101). In an embodiment, the instrument head (101) may also include a magnetic tab (110) that facilitates delivery of the instrument head (101) into the body of a patient, and removal of the instrument head (101) from the body of the patient, using an instrument head delivery and removal device, as disclosed hereinafter. The magnetic tab (110) is movable between an open and closed position, as described below.

Turning now to FIG. 6A, the instrument head (101) is illustrated with a tether (126) and knot (122), and the breakaway member (130) attached to the tether (126). As described above, the tether (126) and knot (122) are engaged by the loop (138) of the retrieval device (154) to couple the instrument head to the instrument assembly (105). FIG. 6B shows the instrument head (101) with an alternative tether configuration, namely, a metallic tether (128) having a hook (124) that can be engaged by the loop (138) of the retrieval device (154). FIG. 6B also shows the magnetic tab (110) in its open position, which causes the instrument head electrode (116) to rotate to its open/use position. From this position cauterizing can take place.

Figure 7:
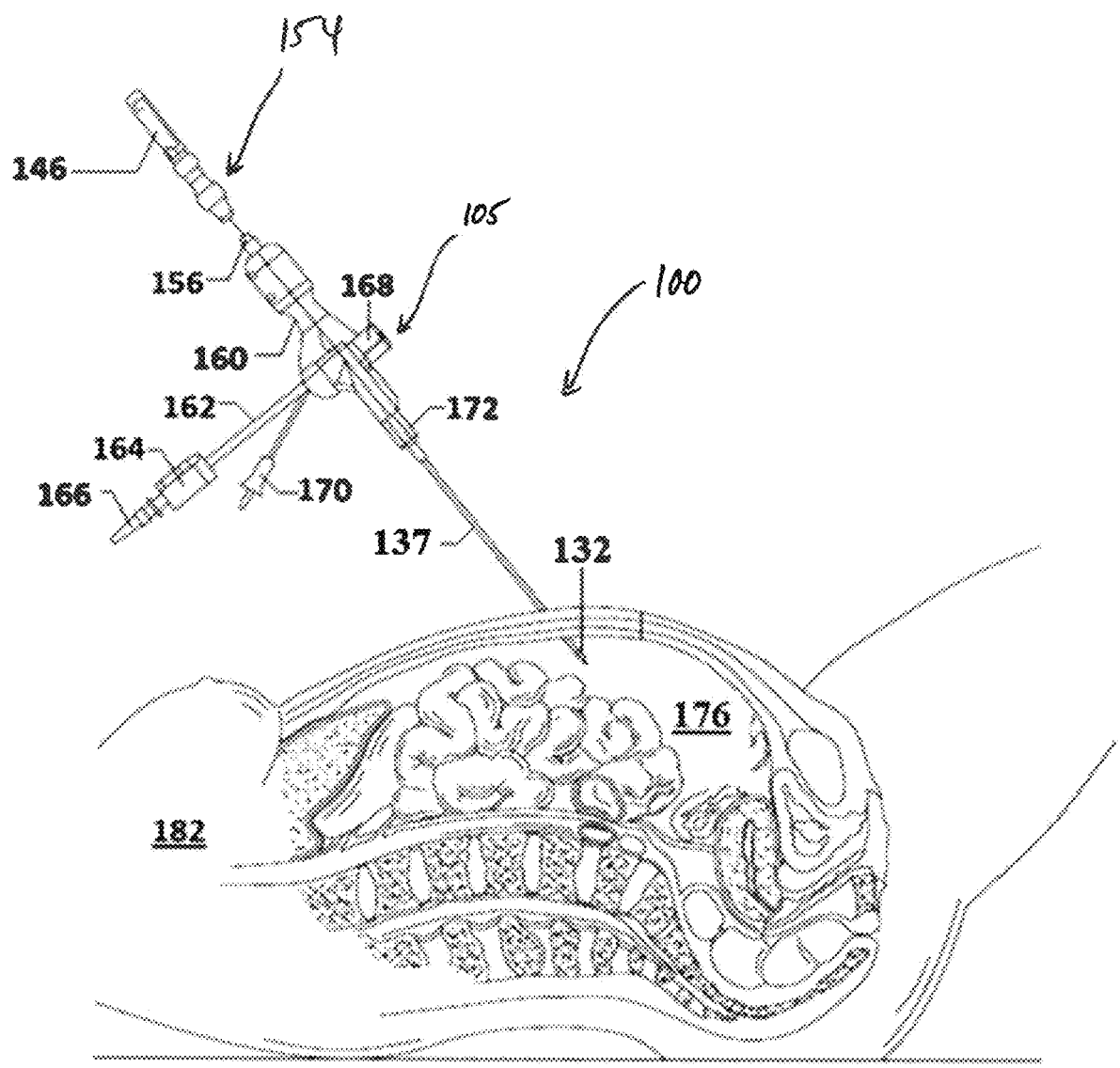
FIG. 7 is a side elevational view of the instrument head retrieval-removal system, showing the piercing the skin of a patient and entering of the abdomen.

With respect to FIG. 7 a clear illustration of the instrument head insertion and removal system (100) is depicted, showing the piercing of the outer skin of a patient (182) with the piercing shaft tip (132) and entering the abdominal cavity (176). The patient (182) is lying down in a typical position as when they are in surgery.

Figure 8:
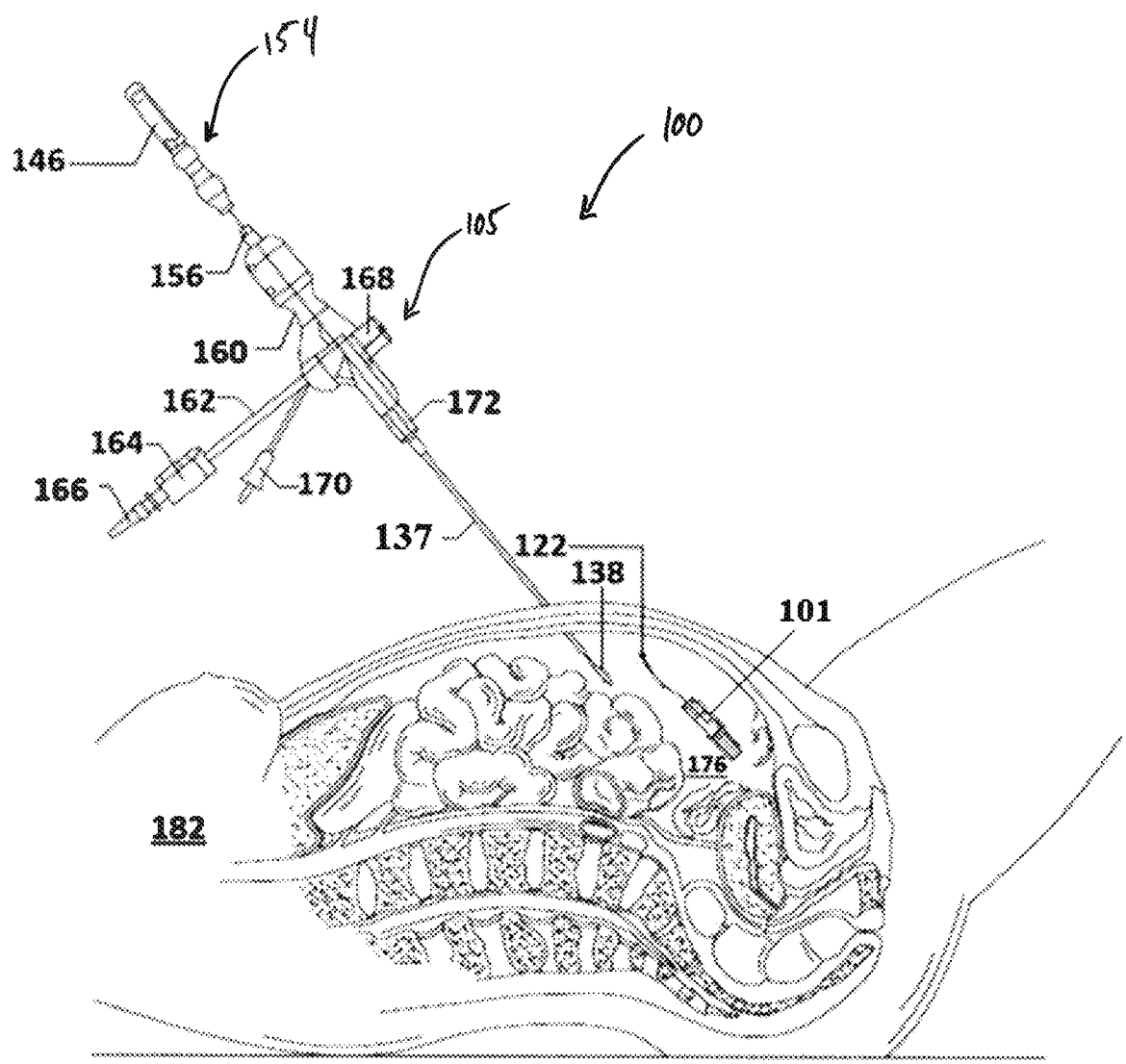
FIG. 8 is a side elevational view of the instrument head retrieval-removal system, showing the grasping loop adjacent to the tether of the instrument head.
Figure 9:
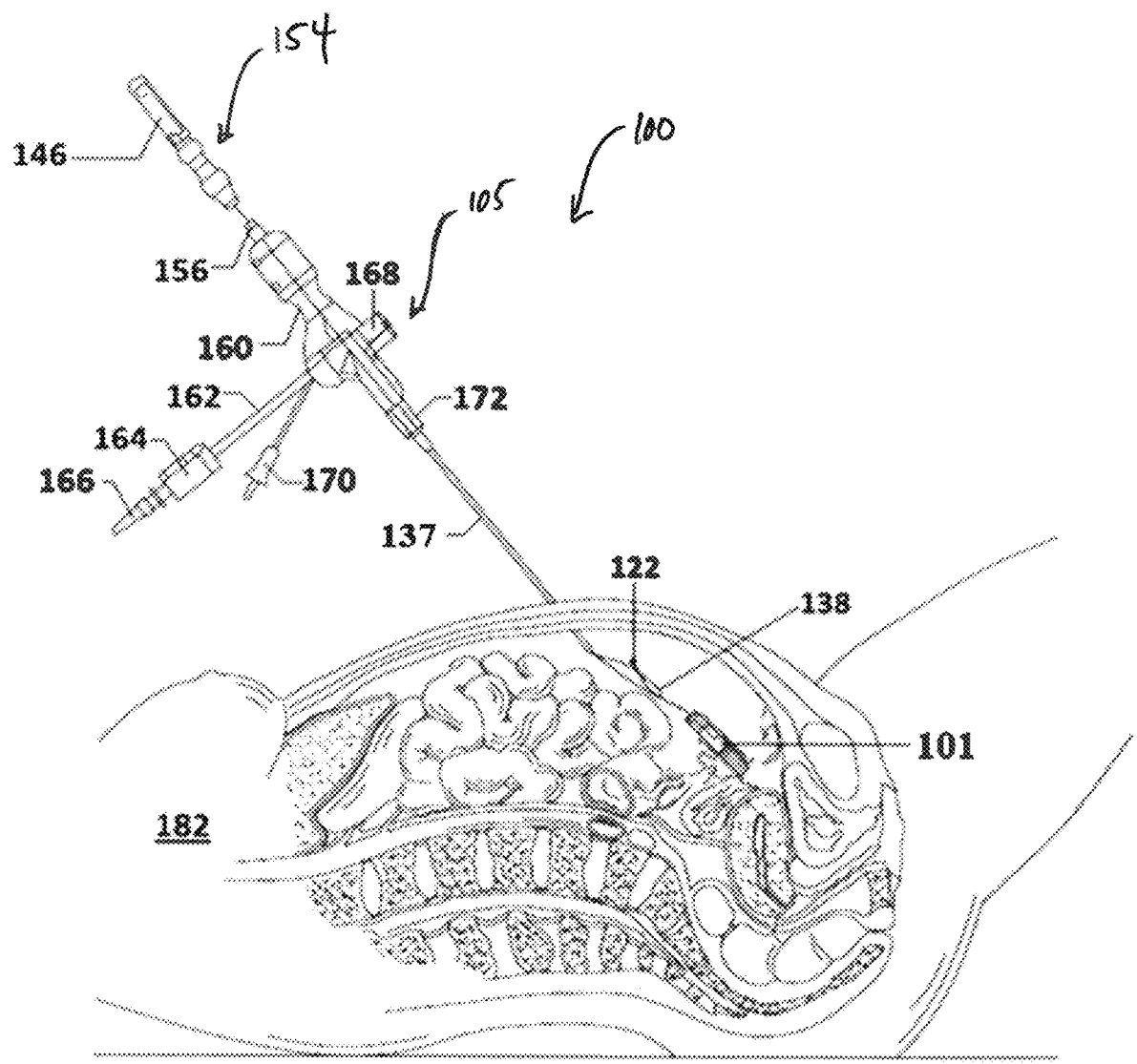
FIG. 9 is a side elevational view of the instrument head retrieval-removal system, showing engagement of the grasping loop with the tether knot, enabling pulling of the instrument head onto the outer shaft of the instrument assembly.

With respect to FIG. 8 a clear illustration of the instrument head insertion and removal system (100) is depicted, but in this instance the distal instrument head (101) has already been inserted through the umbilicus (not shown) to the abdominal cavity (176). Once these two elements (the instrument head (101) and distal ends of the combined retrieval device (154) and instrument assembly (105) are inserted the attachment process described above commences. In particular, as described above, and as shown in FIG. 9, the attachment process begins with the grasping loop (138) being placed around the instrument head (101), particularly around the tether (126) and knot (122) thereof, and pulled by the housing (146) and/or handle portion (151) within the abdominal cavity (176). In particular, once the tether (126) is engaged by the grasping loop (138), the tab 150 may be urged rearwardly to draw the instrument head (101) towards the instrument assembly (105).

Figure 10:
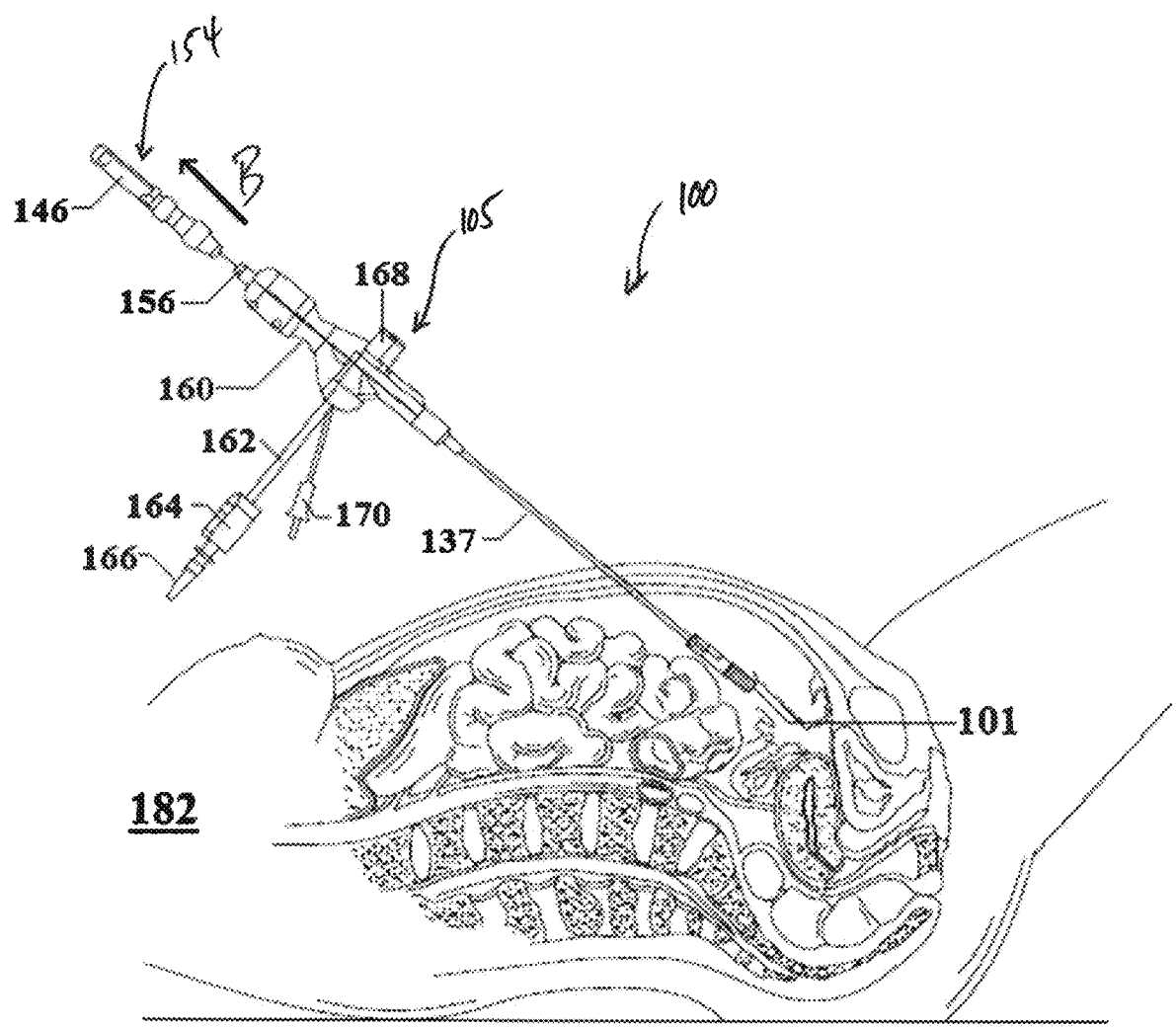
FIG. 10 is a side elevational view of the instrument head retrieval-removal system, showing the instrument head fully attached to the instrument assembly.

With respect to FIG. 10, once the instrument head (101) abuts the distal end of the outer shaft (137), the housing (146) and/or handle portion (153) is pulled rearwardly in the direction of arrow B, in FIG. 10, causing the instrument head assembly (101) to be pulled into the outer shaft (1370), whereby it is coupled and locked to the outer shaft (137) by a coupling/locking mechanism (not shown). In an embodiment, the locking mechanism may be a snap lock, threaded lock, or other similar locking feature. In an embodiment, the threaded portion on a distal end of the instrument shaft can be used to lock the instrument head in place. Other industry-recognized locking means can also be used. Importantly, the string tether (128) is attached at its distal end by the string breakaway member (130), which only breaks away when a greater force than the force needed for attachment is applied. When the instrument head retrieval device (154) is removed from the instrument assembly (105), the tether, after breaking away from the instrument head (101), is removed therewith.

Figure 11A:
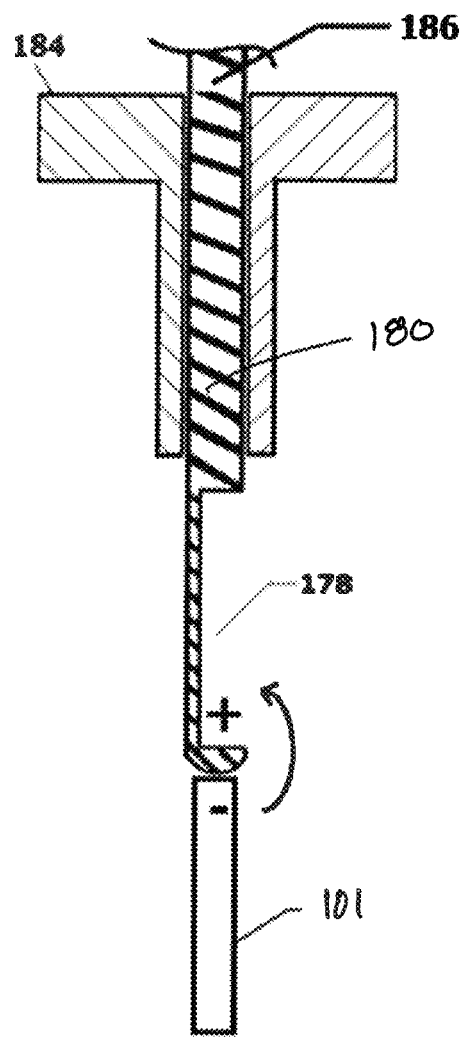
FIG. 11A is a partial cross-sectional view of an instrument head delivery and removal device, that forms a part of the system of FIG. 1.
Figure 11B:
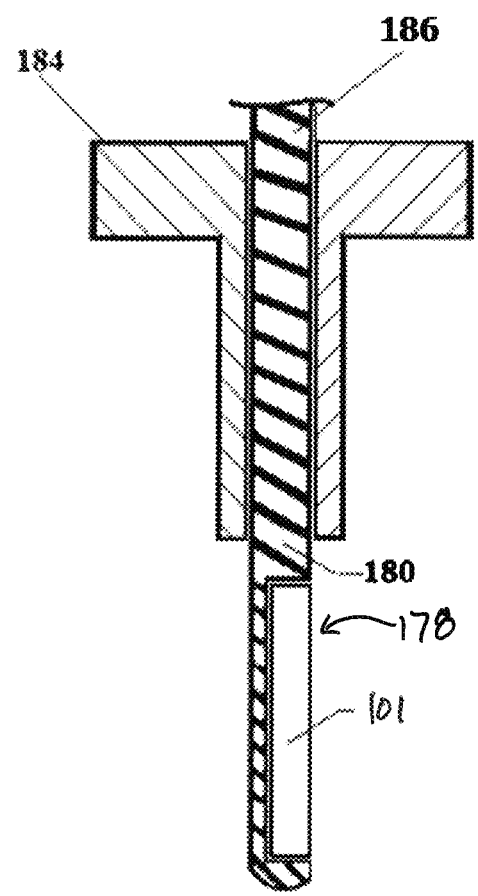
FIG. 11B is another partial cross-sectional view of the instrument head delivery and removal device of FIG. 11A, showing capture of an instrument head.

With respect to FIG. 11A, an instrument head delivery and removal device (186) of the system (100) according to an embodiment of the invention is illustrated. As indicated above, the device (186) is utilized to deliver and remove the instrument head (101) to and from the body of a patient. As shown therein, the device (186) includes a generally cylindrical body (180) having a canopy or cradle (178) formed adjacent to a generally rounded, distal tip thereof. The cradle (178) is dimensioned so as to receive the instrument head (101) therein. The distal end of the body (180) is magnetized with a polarity that is opposite than the polarity of the magnetic tab (110) on the instrument head. When used to remove and instrument head from the body of a patient, the instrument head delivery and removal device (186) is inserted through a trocar (184) positioned near an instrument head (120) whose tip is magnetized of the opposite polarity of the distal tip of the instrument head delivery and removal device (186). When the two devices come within contact, the instrument head (101) flips into the cradle (178) and is held in place ready for removal. FIG. 11B illustrates how the instrument head (101) fits snuggly within the cradle area (178) of the instrument head delivery and removal device (186).

Figure 12:
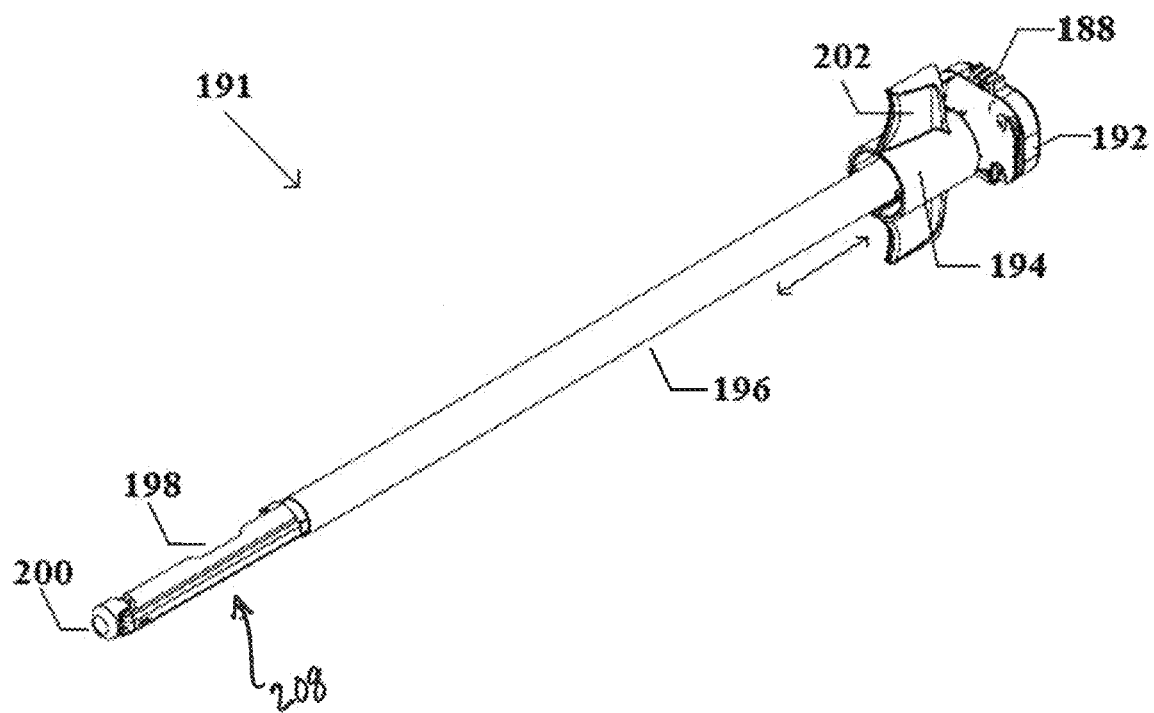
FIG. 12 is a perspective view of an instrument head delivery and removal device according to another embodiment of the present invention.
Figure 13:
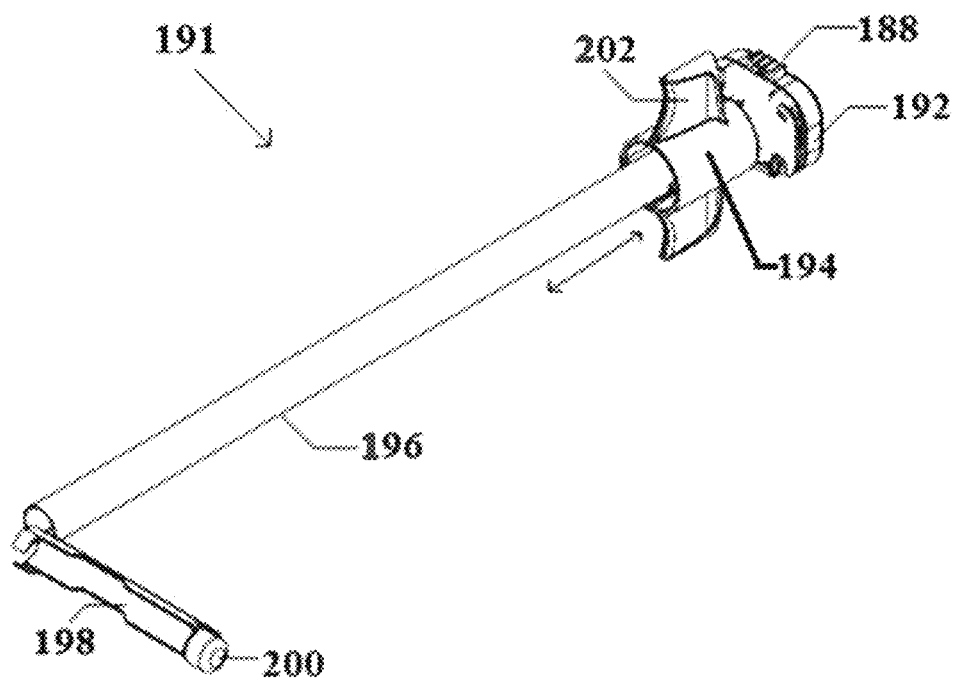
FIG. 13 is a perspective view of the instrument head delivery and removal device of FIG. 12, showing the cradle thereof in an open position.

Tuning to FIGS. 12 and 13, an instrument head delivery and removal device (191) of the system (100) according to an alternative embodiment of the invention is illustrated. The device (191) includes a hollow shaft (196) having a proximal end having an access opining (188), and a distal end to which a cradle (208) having an open side (198) is pivotally connected. As shown therein, the device (191) may also include a finger rest (202) or grasping area and a spring-loaded pivoting actuator (194) on an assembly (192) adjacent to the proximal end. A distal tip (200) of the cradle (208) is magnetized so as to capture the instrument head via the magnetic tab (110). As illustrated in FIG. 13, the actuator (194) is utilized to pivot the cradle from a position where it is longitudinally aligned with the shaft (196) (FIG. 12), to a position where it is oriented approximately 90 degrees with respect to the shaft (196) (FIG. 13), exposing the cradle to capture the instrument head. In particular, squeezing outwardly on the finger rest (202) by a user's fingers causes the pivoting action. The shaft (196) is also used to deliver the tip of the pivoting instrument head delivery retrieval device (191) into the abdominal cavity (176). FIG. 13 shows the pivoting instrument head delivery-retrieval device (191) with the spring-loaded pivoting control (194) compressed, causing the distal tip to bend 90 degrees and exposing the cradle so the instrument head (120) can be inserted.

Importantly, as discussed above, the system and method of the present invention provides for the intra-abdominal assembly and retrieval of laparoscopic instruments and, in particular, the attachment of full size and full function laparoscopic instrument heads to thin instrument shafts. The system and method therefore allows for the quick attachment of oversized instrument heads, which minimizes the scaring and recovery time of the patient, and which overcomes the common problems associated with clogging and other problems associated with longer surgical procedures.

In an embodiment, an instrument head retrieval-removal system for use in a surgical procedure includes an instrument assembly having a hollow shaft, and a grasping mechanism movable between a retracted position wherein the grasping mechanism is housed within the hollow shaft, and an extended position wherein the grasping mechanism extends from a distal end of the hollow shaft to engage an instrument head, wherein after grasping the instrument head, the grasping mechanism is movable to the retracted position to position the instrument head for connection to the instrument assembly. In an embodiment, the system may also include a retrieval device having a hollow inner shaft within which the grasping mechanism is received, wherein the hollow inner shaft of the retrieval device is received within the hollow shaft of the instrument assembly, and wherein a distal tip of the hollow inner shaft of the retrieval device protrudes from a distal end of the hollow shaft of the instrument assembly when the hollow inner shaft of the retrieval device is fully received within the hollow shaft of the instrument assembly. In an embodiment, the grasping mechanism includes a loop configured to engage a tether connected to the instrument head. In an embodiment, the loop has a loop area that expands when it is moved to the extended position. In an embodiment, the loop has one of an oval shape and a diamond shape when in the extended position. In an embodiment, the loop is formed from a wire that is bendable but maintains its shape when in the extended position. In an embodiment, the grasping mechanism includes a shaft connected to the loop and received within the hollow inner shaft of the retrieval device, and an actuator connected to the shaft adjacent to a proximal end of the retrieval device, for selectively moving the grasping mechanism between the retracted position and the extended position. In an embodiment, the hollow inner shaft of the retrieval device is insertable into a proximal opening of the instrument assembly. In an embodiment, the instrument assembly includes at least one tube connectable to least one of a suction source and/or an irrigation source, and at least one knob for selectively controlling suction and/or irrigation. In an embodiment, the system also includes the instrument head, the instrument head including a breakaway member, wherein the tether is connected to the breakaway member, and wherein the breakaway member and the tether are configured to decoupled from the instrument head when the loop is pulled through the hollow inner shaft of the retrieval device. In an embodiment, the instrument head includes a body portion and a foam material on the body portion for retaining a lens cleaning solution. In an embodiment, the instrument head includes a magnetic tab for engagement with an instrument head delivery and removal device. In an embodiment, the system includes the instrument head delivery and removal device, the instrument head retrieval and removal device including a shaft and a cradle arranged at a distal end of the shaft, wherein a distal end of the cradle is magnetized so as to engage the instrument head via the magnetic tab. In an embodiment, the cradle is pivotable approximately 90 degrees with respect to the shaft of the instrument head retrieval and removal device.

In another embodiment, a method for attaching an instrument head to an instrument within a body of a patient includes delivering an instrument head having a tether into a body of a patient, inserting a hollow instrument shaft into the body of the patient and positioning a distal end of the instrument shaft adjacent to the instrument head, extending a grasping mechanism from the instrument shaft, engaging the tether with the grasping mechanism, and retracting the grasping mechanism into the instrument shaft to draw the instrument head into abutting relationship with the instrument shaft. The method may further include the steps of connecting the instrument head to the instrument shaft and withdrawing the grasping mechanism from the instrument shaft, wherein when the grasping mechanism is withdrawn from the instrument shaft, the tether decouples from the instrument head and is removed with the grasping mechanism from the instrument shaft. Additionally, the method may include inserting a retrieval device having a hollow inner shaft into the instrument shaft, wherein the grasping mechanism is received within the hollow inner shaft of the retrieval device. In an embodiment, the grasping mechanism is a wire or string loop.

In yet another embodiment, an instrument head retrieval-removal system for use in a surgical procedure includes an instrument head delivery and removal device, the instrument head retrieval and removal device including a shaft and a cradle arranged at a distal end of the shaft, wherein a distal end of the cradle is magnetized so as to engage the instrument head via a magnetic tab on the instrument head such that the instrument head rotates into the cradle, wherein the cradle is pivotable approximately 90 degrees with respect to the shaft, and wherein the shaft is insertable into a patient through an incision or trocar to deliver the instrument head. In an embodiment, the system further includes an instrument assembly having a hollow shaft, and a grasping mechanism movable between a retracted position wherein the grasping mechanism is housed within the hollow shaft, and an extended position wherein the grasping mechanism extends from a distal end of the hollow shaft to engage a tether of the instrument head, wherein after grasping the instrument head, the grasping mechanism is movable to the retracted position to position the instrument head for connection to the instrument assembly.

Although this invention has been shown and described with respect to the detailed embodiments thereof, it will be understood by those of skill in the art that various changes may be made and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the particular embodiments disclosed in the above detailed description, hut that the invention will include all embodiments falling within the scope of this disclosure.

What is claimed is:

1. An instrument head retrieval-removal system for use in a surgical procedure, comprising:
   an instrument assembly having a hollow shaft; and
   a retrieval device having a hollow inner shaft, the hollow inner shaft of the retrieval device being slidably received within the hollow shaft of the instrument assembly; and
   an instrument head the instrument head including a breakaway member and a tether connected to the breakaway member;
   wherein the retrieval device further includes a shaft slidably received within the hollow inner shaft of the retrieval device and a grasping mechanism connected to the shaft of the retrieval device, the grasping mechanism including a loop configured to engage a tether connected to the instrument head;
   wherein the grasping mechanism is movable between a retracted position wherein the grasping mechanism is housed within the hollow inner shaft of the retrieval device, and an extended position wherein the grasping mechanism extends from a distal end of the hollow inner shaft of the retrieval device and the hollow shaft of the instrument assembly to engage an instrument head;
   wherein after grasping the instrument head, the grasping mechanism is movable to the retracted position to position the instrument head for connection to the hollow shaft of the instrument assembly;

wherein the breakaway member and the tether are configured to decouple from the instrument head when the loop is pulled through the hollow inner shaft of the retrieval device; and wherein the hollow shaft of the instrument assembly is configured for connection with the instrument head.

2. The instrument head retrieval-removal system of claim 1, wherein:

a distal tip of the hollow inner shaft of the retrieval device protrudes from a distal end of the hollow shaft of the instrument assembly when the hollow inner shaft of the retrieval device is fully received within the hollow shaft of the instrument assembly.

3. The instrument head retrieval-removal system of claim 1, wherein:

the loop has a loop area that expands when it is moved to the extended position.

4. The instrument head retrieval-removal system of claim 3, wherein:

the loop has one of an oval shape and a diamond shape when in the extended position.

5. The instrument head retrieval-removal system of claim 4, wherein:

the loop is formed from a wire that is bendable but maintains its shape when in the extended position.

6. The instrument head retrieval-removal system of claim 1, wherein:

the grasping mechanism includes a shaft connected to the loop and received within the hollow inner shaft of the retrieval device, and an actuator connected to the shaft adjacent to a proximal end of the retrieval device, for selectively moving the grasping mechanism between the retracted position and the extended position.

7. The instrument head retrieval-removal system of claim 6, wherein:

the hollow inner shaft of the retrieval device is insertable into a proximal opening of the instrument assembly.

8. The instrument head retrieval-removal system of claim 1, wherein:

the instrument assembly includes at least one tube connectable to at least one of a suction source and/or an irrigation source, and at least one knob for selectively controlling suction and/or irrigation.

9. The instrument head retrieval-removal system of claim 1, wherein:

the instrument head includes a body portion and a foam material on the body portion for retaining a lens cleaning solution.

10. The instrument head retrieval-removal system of claim 1, wherein:

the instrument head includes a magnetic tab.

11. The instrument head retrieval-removal system of claim 1, wherein:

the retrieval device further includes a spring-loaded actuator connected to the grasping mechanism by the shaft of the retrieval device, the spring-loaded actuator being configured to move the grasping mechanism at least one of into and/or out of the hollow shaft of the retrieval device.

12. The instrument head retrieval-removal system of claim 1, wherein:

a distal end of the shaft of the retrieval device is magnetized.

13. An instrument head retrieval-removal system for use in a surgical procedure, comprising:

an instrument assembly having a hollow shaft;

a grasping mechanism including a loop; and an instrument head, the instrument head including a breakaway member and a tether connected to the breakaway member;

wherein the loop is movable between a retracted position wherein the loop is housed within the hollow shaft, and an extended position wherein the loop extends from a distal end of the hollow shaft to engage the tether of the instrument head;

wherein after grasping the instrument head, the loop is movable to the retracted position to position the instrument head for connection to the instrument assembly; and wherein the breakaway member and the tether are configured to decouple from the instrument head when the grasping mechanism is removed from the hollow shaft of the instrument assembly.

\* \* \* \* \*